(12) United States Patent
vom Endt et al.

(10) Patent No.: US 11,754,651 B2
(45) Date of Patent: Sep. 12, 2023

(54) PATIENT-MODEL-BASED DETERMINATION OF A STIMULATION OF A MAGNETIC RESONANCE IMAGING

(71) Applicants: Siemens Healthcare GmbH, Erlangen (DE); The General Hospital Corporation, Boston, MA (US)

(72) Inventors: Axel vom Endt, Erlangen (DE); Peter Dietz, Fürth (DE); Andreas Krug, Fürth (DE); Mathias Davids, Cambridge, MA (US); Lawrence Wald, Cambridge, MA (US)

(73) Assignees: Siemens Healthcare GmbH, Erlangen (DE); The General Hospital Corporation, Boston, MA (US)

( * ) Notice: Subject to any disclaimer, the term of this patent is extended or adjusted under 35 U.S.C. 154(b) by 0 days.

(21) Appl. No.: 17/555,698

(22) Filed: Dec. 20, 2021

(65) Prior Publication Data

US 2022/0221541 A1    Jul. 14, 2022

Related U.S. Application Data

(60) Provisional application No. 63/135,000, filed on Jan. 8, 2021.

(51) Int. Cl.
  *G01R 33/54* (2006.01)
  *A61B 5/055* (2006.01)
  *G01R 33/385* (2006.01)

(52) U.S. Cl.
  CPC ............ *G01R 33/543* (2013.01); *A61B 5/055* (2013.01); *G01R 33/385* (2013.01)

(58) Field of Classification Search
  CPC ...... G01R 33/543; G01R 33/385; A61B 5/055
  See application file for complete search history.

(56) References Cited

U.S. PATENT DOCUMENTS

2010/0113959 A1*  5/2010  Pascual-Leone ...... A61N 2/008
                                                                    600/13

FOREIGN PATENT DOCUMENTS

| JP | 2020531228 A | * 11/2020 | ............ G06V 40/168 |
| JP | 2020533103 A | * 11/2020 | ............. A61B 5/055 |
| WO | WO-2019050225 A1 | * 3/2019 | ............ A61B 5/0035 |

OTHER PUBLICATIONS

Davids, Mathias, et al. "Predicting magnetostimulation thresholds in the peripheral nervous system using realistic body models." Scientific reports 7.1 (2017): 1-14.

(Continued)

*Primary Examiner* — Dixomara Vargas
(74) *Attorney, Agent, or Firm* — Lempia Summerfield Katz LLC

(57) ABSTRACT

A method for determining peripheral nerve stimulation during MR imaging of a patient in a MR scan unit for a MR pulse sequence is described. In the method, a plurality of model-based candidate stimulations are determined dependent on a unit vector potential of the gradient magnet field generated during MR imaging and dependent on candidate data models for different object parameter values. A model-based candidate data stimulation is selected as a stimulation model for the patient dependent on an individual patient model. A distribution of a vector potential of a gradient magnetic field acting on the patient is determined as a function of a unit gradient current for a determined position of the patient in the MR scanning unit. The nerve stimulation of the patient is determined for the determined position based on the selected candidate stimulation and a gradient current of a gradient pulse of the MR pulse sequence.

19 Claims, 6 Drawing Sheets

(56) References Cited

OTHER PUBLICATIONS

Davids, Mathias, et al. "Prediction of peripheral nerve stimulation thresholds of MRI gradient coils using coupled electromagnetic and neurodynamic simulations." Magnetic resonance in medicine 81.1 (2019): 686-701.

Davids, Mathias, et al. "Prediction of peripheral nerve stimulation thresholds of MRI gradient coils using coupled electromagnetic and neurodynamic simulations." Magnetic resonance in medicine (2018): 1-16.

* cited by examiner

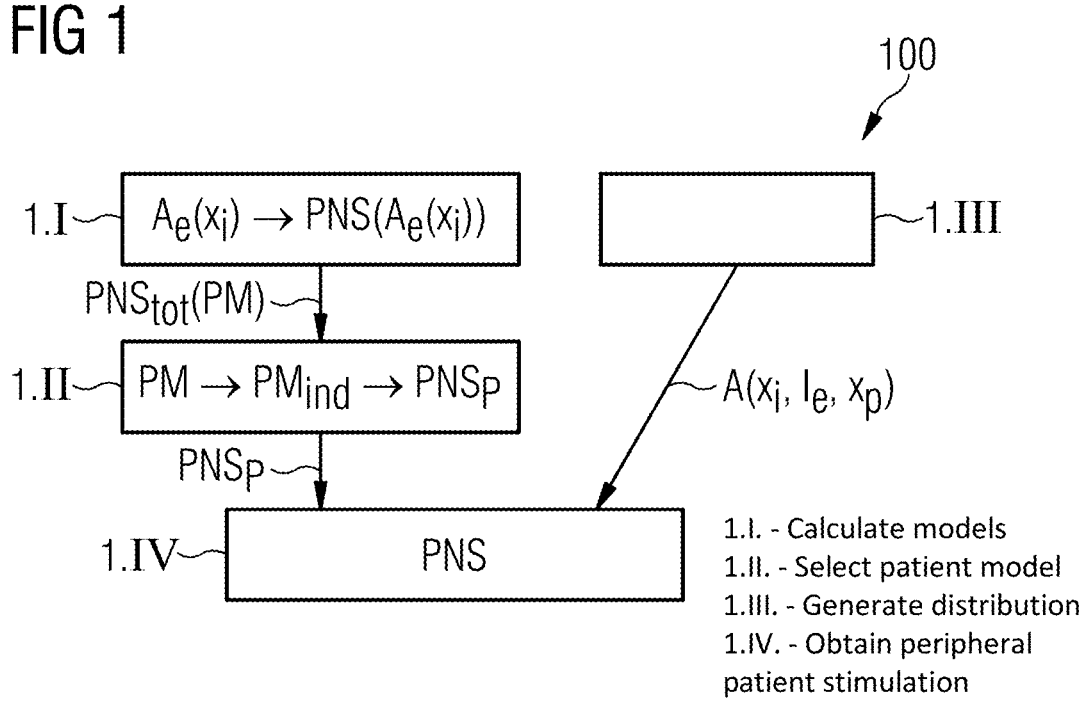
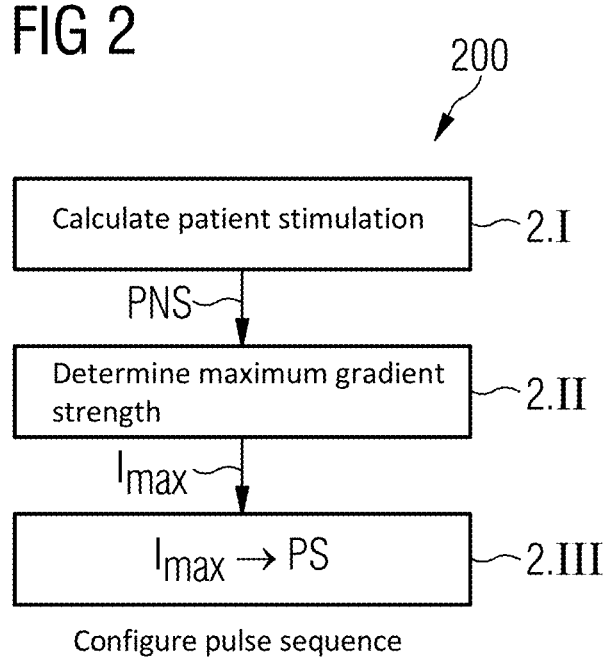

40 Stimulation detection device
41 Candidate model determination unit
41a Data storage
42 Selection unit
43 Vector potential determination unit
44 Stimulation determination unit 40 Stimulation detection device
50 Pulse sequence optimization device
51 Input interface
52 Gradient strength determination unit
53 Pulse sequence optimization unit

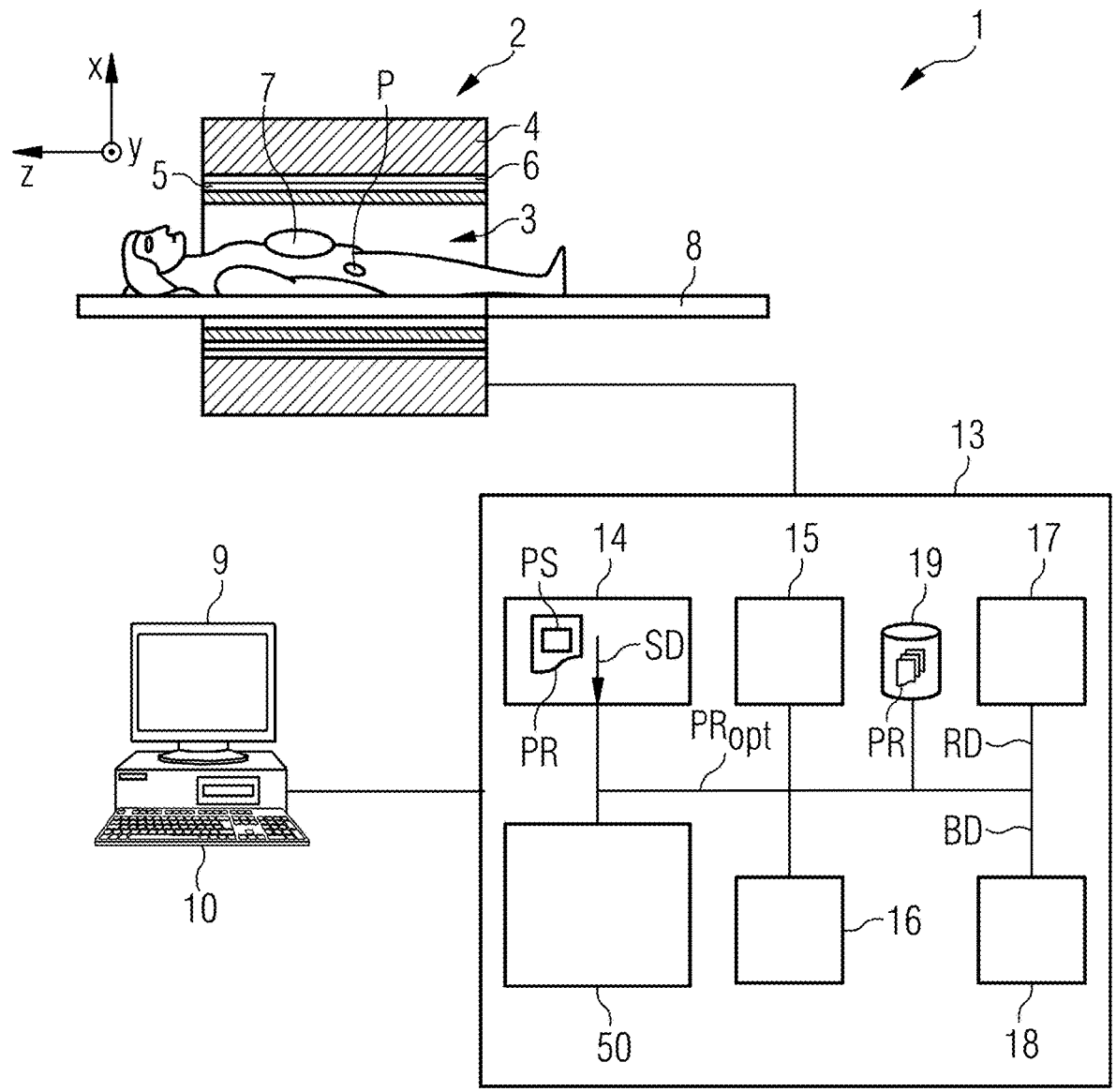

FIG 6

1 Magnetic resonance system
2 MR scanning unit
3 Examination zone
4 Basic field magnet system
5 RF transmission antenna system
6 Gradient system
7 RF receiving antenna system
8 Bed
9 Display unit
10 Input unit 13 Central control device
14 Sequence control unit
15 Radio frequency transmitter
16 Gradient system interface
17 Radio frequency receiving equipment
18 Reconstruction unit
19 Memory
50 Pulse sequence optimization device

PATIENT-MODEL-BASED DETERMINATION OF A STIMULATION OF A MAGNETIC RESONANCE IMAGING

The present patent document claims the benefit of U.S. Provisional Patent Application No. 63/135,000, filed Jan. 8, 2021, which is hereby incorporated by reference in its entirety.

TECHNICAL FIELD

The disclosure relates to a method for determining a peripheral nerve stimulation during magnetic resonance (MR) imaging of a patient in a MR scanning unit for a MR pulse sequence, a gradient strength determination method, a magnetic resonance imaging method, a stimulation determination device, a pulse sequence optimization device, and a magnetic resonance imaging system.

BACKGROUND

With the help of modern imaging processes, two- or three-dimensional image data may be generated that may be used to visualize an imaged patient and also for other applications.

In a magnetic resonance system, also called a magnetic resonance imaging system, the body to be examined may be exposed to a relatively high basic magnetic field, for example of 1, 3, 5, or 7 Tesla, with aid of a basic field magnet system. In addition, a magnetic field gradient is created with the help of a gradient system. High-frequency excitation signals (RF signals) are then transmitted via a high-frequency transmission system using suitable antenna devices, which may lead to the nuclear spins of certain atoms resonantly excited by this high-frequency field by a defined flip angle relative to the magnet field lines of the basic magnetic field are tilted. During the relaxation of the nuclear spins, high-frequency signals, so-called magnetic resonance signals, are emitted, which are received by suitable receiving antennas and then processed further. The desired image data may then be reconstructed from the raw data acquired in this way.

For a specific measurement, a specific pulse sequence is to be transmitted, which includes a sequence of high-frequency pulses, in particular excitation pulses and refocusing pulses, as well as gradient pulses to be transmitted in different spatial directions in a coordinated manner. Readout windows are set at the appropriate time, which specify the time periods in which the induced magnetic resonance signals are recorded. In particular, the timing within the sequence is decisive for the imaging, e.g., in which time intervals which pulses follow one another. A large number of the control parameters may be defined in a so-called measurement protocol, which is created in advance and, for example, may be called up from a memory for a specific measurement and, if necessary, changed by the operator on site, who may specify additional control parameters, such as a distance of layers of a stack of layers to be measured, a layer thickness, etc. A pulse sequence, (also referred to as a measurement sequence), is then calculated based on all of these control parameters.

In magnetic resonance imaging, no direct image recording takes place in spatial space, but magnetic resonance signals are first measured, the amplitude of which may be interpreted as a Fourier transform of the image recording in k-space. The k-space is the spatial frequency space of the density distribution of the magnetic moments in an area to be examined in which MR signals are recorded. If the k-space is scanned adequately, the spatial distribution of the density of the magnetic moments is obtained by a (two-dimensional) Fourier transformation (in case of acquisition in layers). During the measurement, this k-space is filled with raw data corresponding to the acquired magnetic resonance signals. Predetermined trajectories, (e.g., the lines on a Cartesian grid), of k-space are conventionally scanned.

During a MR imaging process, a patient is exposed to magnetic fields that vary over time, in particular gradient fields. These gradient fields induce electrical fields in the patient's body, so that the patient experiences a stimulation of his peripheral nerves. Such a stimulation may manifest itself in sensed stimuli and involuntary movements, which reduces patient comfort and the image quality of a MR image may be impaired due to patient movements. In order to avoid the stimulation, the gradient amplitudes are limited by a monitoring device. The actual extent of a patient's stimulation depends on the constitution, (e.g., the weight, size, and distribution of fat and muscles), and also on the position of the patient within the scan unit, (e.g., the position of the patient in the gradient field). If the patient stimulation is not determined precisely, however, the gradient performance of a MR system may be unnecessarily restricted, so that the image quality achieved in a MR-imaging is not optimal.

Conventionally, the stimulation is limited by a stimulation monitor. This monitor is based on a stimulation study. During such a study, a statistically relevant number of volunteer test subjects are exposed to identical gradient pulses in a MR system and the occurrence of the stimulation is measured. The level of stimulation varies between the different subjects participating in the study. The parameters for the stimulation monitor are defined in such a way that only a certain percentage of the test subjects experience stimulation. However, such a monitor neither takes into account the different stimulation of individual patients nor the position dependency of the peripheral nerve stimulation, also abbreviated to "PNS".

Consequently, there is a problem in achieving an optimal image quality for an individual patient in the context of MR imaging without causing peripheral nerve stimulation.

SUMMARY AND DESCRIPTION

This object is achieved by a method for determining a peripheral nerve stimulation during MR imaging of a patient in a MR scan unit for a MR pulse sequence, a gradient strength determination method, a magnetic resonance imaging method, a stimulation determination device, a pulse sequence optimization device, and a magnetic resonance imaging system as described herein. The scope of the present disclosure is defined solely by the appended claims and is not affected to any degree by the statements within this summary. The present embodiments may obviate one or more of the drawbacks or limitations in the related art.

In the method for determining a peripheral nerve stimulation during MR imaging of a patient in a MR scan unit for a MR pulse sequence, a plurality of model-based candidate stimulations or candidate stimulation models are determined. Such a patient may be a human or an animal. The stimulation values predicted by the candidate stimulation models are determined as a function of a unit vector potential of a gradient magnetic field generated during MR imaging and candidate models for different object parameter values. Such object parameter values include parameter values that influence the individual response of a patient to a gradient magnetic field. Examples of this are the muscle percentage, the fat percentage, the BMI (Body Mass Index), and similar parameters.

The calculation of a stimulation of the peripheral nervous system of a person is described in Davids M, Guerin B, Sch L R, Wald L L. "Predicting magnetostimulation thresholds in the peripheral nervous system using realistic body models", Sci Rep. 2017; 7: 5316 and Davids M, Guerin B, Endt A, Schad L R, Wald L L. "Prediction of peripheral nerve stimulation thresholds of MRI gradient coils using coupled electromagnetic and neurodynamic simulations", Magn Reson Med. 2019; 81: 686-701.

Within the scope of the method, a model-based candidate stimulation is also selected as a stimulation model for a specific patient for whom MR imaging is to be carried out, depending on an individual patient model for the patient, which is determined dependent on the object parameter values of the patient. Furthermore, a distribution of a vector potential acting on the patient of the gradient magnetic field generated during the MR imaging is determined as a function of a unit gradient current for a determined position of the patient in the MR scanning unit. If necessary, the vector potential may also be determined as a function of the determined or selected individual patient model.

The nerve stimulation of the patient is determined for the determined position of the patient based on the selected candidate stimulation and the determined vector potential acting on the patient, which is or would be caused by a unit gradient current, as well as based on the actual gradient current of a gradient pulse of the MR pulse sequence.

A great advantage of the procedure is the calculation of candidate sets for a peripheral stimulation response to a unit vector potential of a magnetic field. Because the candidate rates only have to be calculated once, the candidate sets may then be kept in a database. The candidate sets may advantageously be used for a large number of different pulse sequences, because the unit vector potential does not depend on specific gradients. Directly before imaging with an individual patient, a model for the patient is then generated based on object-specific parameter values, (e.g., patient parameter values), and on this basis, a suitable data set for a stimulation response to a unit vector potential may be selected. The stimulation response is determined as a data set of discrete location-dependent values, which may be evenly distributed over an area surrounding an examination area. If none of the stored stimulation response models fit exactly, it is also possible to interpolate between two data sets in order to generate a more precisely adapted stimulation response model. The candidate sets are therefore in particular independent of a specific pulse sequence, a gradient strength, and a position of a patient in a scan unit.

Since the extensive calculations for this may be carried out in advance, they are not time-critical for imaging. The vector potential is also calculated in advance and stored in a database in matrix form. In this case, the vector potential is calculated for different patient positions. Shortly before the actual imaging, a suitable data set of the vector potential may then be selected, which is assigned to an actual patient position in a MR scanning unit. With this selection, too, an interpolation between two data sets may be carried out if none of the data sets is assigned exactly to the actual position of the patient. The vector potential is also determined as a data set of discrete, location-dependent values, which may be evenly distributed over an area surrounding the patient. Advantageously, only a simple matrix operation, (e.g., a matrix multiplication), has to be carried out directly before the MR imaging in order to determine an individual peripheral stimulation of a patient. This saves time compared to a conventional procedure in which the entire calculation of an individual patient stimulation is carried out shortly before the imaging dependent on individual parameters, such as patient parameters, and an individual position of the patient in the scan unit of a MR system and the gradient of a MR pulse sequence used for individual imaging. The individual pulse sequence is included as a third factor in the calculation of the patient's individual nerve stimulation in the form of a gradient current of a gradient in the MR pulse sequence.

A gradient strength of a protocol of a MR imaging method may advantageously be changed or adapted by modifying a gradient current as a function of the calculated peripheral nerve stimulation in such a way that predetermined maximum values of the peripheral nerve stimulation are not exceeded, but on the other hand a sufficient, (e.g., a maximum), gradient strength that is just compatible with the desired patient comfort or the individual response behavior of the patient to nerve stimulation, at which an image quality is optimal, is achieved.

In the gradient strength determination method, a patient stimulation dependent on a gradient strength is determined by the method for determining peripheral nerve stimulation during MR imaging of a patient in a MR scan unit for a MR Pulse sequence. Then an allowed, maximum gradient strength of the pulse sequence is determined, at which an allowed maximum patient stimulation is not exceeded. Finally, the pulse sequence is configured to the determined, permitted maximum gradient strength. As already indicated, this approach saves considerable time in the initial phase of MR imaging, so that the patient does not have to wait so long in the scanning unit and, moreover, an increased throughput of imaging processes is achieved, which means valuable medical resources may be used more efficiently.

In the magnetic resonance imaging method, a pulse sequence is first generated by the gradient strength determination method. Then an area of a patient to be examined is stimulated by the generated pulse sequence and magnetic resonance signals are recorded. Finally, image data are reconstructed based on the acquired magnetic resonance signals or the raw data resulting therefrom. The magnetic resonance imaging method shares the advantages of the method for determining peripheral nerve stimulation during MR imaging of a patient in a MR scan unit for a MR pulse sequence and the gradient strength determination method.

The stimulation determination device has a candidate model determination unit for determining a plurality of model-based candidate stimulations as a function of a unit vector potential and candidate models for different patients. Part of the stimulation determination device is also a selection unit for selecting a model-based candidate stimulation as a stimulation model for an individual patient as a function of an individual patient model for the patient, which is determined as a function of the patient's object parameter values. The stimulation determination device also includes a vector potential determination unit for determining a distribution of a vector potential of the gradient magnetic field acting on the patient generated during MR imaging as a function of a unit gradient current for a determined position of the patient in the MRI scanning unit. In addition, the stimulation determination device includes a stimulation determination unit for determining a nerve stimulation of the patient for the determined position based on the selected candidate stimulation, the determined vector potential, acting on the patient and a gradient current of a gradient pulse of the MR pulse sequence. The stimulation determination device shares the advantages of the method for determining peripheral nerve stimulation during MR imaging of a patient in a MR scan unit for a MR pulse sequence during magnetic resonance imaging.

The pulse sequence optimization device has an input interface for receiving parameter values of a patient and position information relating to the position of the patient in a scanner in a MR system. In addition, the pulse sequence optimization device includes a stimulation determination device which is set up to determine an individual nerve stimulation of a patient for the position of the patient. Furthermore, the pulse sequence optimization device also has a gradient strength determination unit for determining a maximum gradient current strength of the pulse sequence, at which an allowed maximum patient stimulation is not exceeded, based on the determined patient stimulation. Part of the pulse sequence optimization device is also a pulse sequence optimization unit for adapting the pulse sequence to the determined maximum gradient strength based on the determined maximum gradient current strength. The pulse sequence optimization device shares the advantages of the pulse sequence optimization method.

The magnetic resonance imaging system includes a radio-frequency transmission system, a gradient system, and a control device. The control device is designed to control the high-frequency transmission system and the gradient system in order to carry out a desired measurement based on a predetermined pulse sequence. The magnetic resonance imaging system also includes a pulse sequence optimization device. The magnetic resonance imaging system shares the advantages of the magnetic resonance imaging method.

Components of the stimulation determination device and the pulse sequence optimization device may be configured in the form of software components. This applies in particular to the candidate model determination unit, the selection unit, the pulse sequence optimization unit, the vector potential determination unit, the stimulation determination unit, the gradient strength determination unit, and the pulse sequence optimization unit, but also interfaces of the stimulation determination device and the pulse sequence optimization device. In principle, however, some of these components may also be implemented in the form of software-supported hardware, (e.g., field-programmable gate arrays or the like), especially when it comes to particularly fast calculations. Likewise, the required interfaces, (e.g., if it is only a matter of transferring data from other software components), may be configured as software interfaces. However, they may also be configured as hardware-based interfaces that are controlled by suitable software.

In particular, the stimulation determination device and the pulse sequence optimization device may be part of a user terminal of a MR system or part of software installed therein.

A largely software-based implementation has the advantage that magnetic resonance imaging systems that have already been used may easily be retrofitted by a software update in order to work in the manner. In this respect, the object is also achieved by a corresponding computer program product with a computer program that may be loaded directly into a memory device, (e.g., a control device of a magnetic resonance imaging system), with program sections, in order to carry out all acts of the method for determining a peripheral nerve stimulation during MR imaging of a patient in a MR scan unit for a MR pulse sequence or the gradient strength determination method, when the program is executed in the magnetic resonance imaging system, in particular the control device. In addition to the computer program, such a computer program product may contain additional components such as a documentation and/or additional components, including hardware components such as hardware keys (e.g., dongles, etc.) for using the software.

For transport to the magnetic resonance imaging system or to the control device of the magnetic resonance imaging system and/or for storage on or in the magnetic resonance imaging system or the control device of the magnetic resonance imaging system, a computer-readable medium, (e.g., a memory stick, a hard disk, or some other transportable or permanently installed data carrier), is used on which the program sections of the computer program that may be read in and executed by a computer unit of the magnetic resonance imaging system or the control device are stored. The computer unit may include one or more cooperating microprocessors or the like used for this purpose.

In the method for determining a peripheral nerve stimulation during MR imaging of a patient in a MR scanning unit for a MR pulse sequence for determining the model-based candidate stimulation, a virtual interface cylinder may be placed around a patient model or a modeled patient and location-dependent stimulation values are determined for partial areas of the virtual interface cylinder. In this context, "placed around" the patient is intended to mean that the longitudinal axis of this virtual interface cylinder runs in the direction of the longitudinal axis of a patient lying in the scanning unit of a MR system and the cylinder jacket of the virtual interface cylinder is located outside the patient's body or surrounds the patient's body, but is positioned inside the cavity of the scanning unit, so that a magnetic field generated by the electromagnets of the scanning unit, in particular a gradient magnetic field, penetrates the cylinder jacket. Such a cylinder jacket may advantageously be divided into individual partial areas, (e.g., grid areas), to each of which a unit vector potential may be assigned, which is used to calculate a nerve stimulation, which is initially independent of the patient's position and thus independent of the magnetic field distribution, but dependent of a patient-model-dependent of a patient.

In certain examples, the determined model-based candidate stimulations, from which a suitable patient-specific stimulation model is selected for an individual patient, may be determined based on the sum of the candidate stimulations assigned to the individual partial areas of the virtual interface cylinder. A total value of a nerve stimulation acting on the patient is advantageously determined, which may be compared with a predetermined threshold value in order to adapt a gradient strength and thus a pulse sequence used in MR imaging or a sequence protocol assigned to this pulse sequence.

The majority of the model-based candidate stimulations may be generated once in advance and are then stored, applicable to any differently parameterized MR imaging, which may be carried out with a different rate of increase of gradient pulses, with pulses with different lengths, with different pulse frequencies, or with pulses with a different pulse shape. These data may advantageously be calculated and stored in advance so that they are available for MR imaging at any time. The calculations required for this are therefore not critical for the time required for MR imaging. Advantageously, a gradient strength may be adjusted in a shorter time compared to conventional approaches. Since the patient's position in a scan unit is known for the adjustment, the patient is in the scan unit for the above-mentioned preparatory measures, especially during the calculation of an individual patient stimulation. Advantageously, by the procedure and as a result of the shortened calculation time for an individual patient stimulation the time in which the patient has to remain calm in the scanning unit, is reduced. In addition, reducing the occupancy time of the MR system by a patient increases the overall capacity of the MR system for a certain number of possible imaging processes in a certain time.

In the method for determining a peripheral nerve stimulation during MR imaging of a patient in a MR scanning unit for a MR pulse sequence, an individual patient model may be generated as a function of at least one of the following parameters: the size of the patient, the patient's weight, the patient's fat distribution, the muscle distribution of the patient, the patient's body mass index, and/or the patient's sex.

The mentioned parameters influence the strength of a peripheral nerve stimulation in a patient. A patient model may advantageously be individualized as a function of these parameters, so that a more precise prognosis of a nerve stimulation of the patient may be made.

The stimulation of the individual patient for the determined position may be determined by multiplying the selected candidate stimulation with the determined vector potential acting on the patient, caused by the gradient current of a gradient pulse of the MR pulse sequence. The vector potential acting on the patient results from a vector potential based on a unit gradient current multiplied by the actual gradient current for a certain MR pulse sequence or a gradient pulse played out with such a MR pulse sequence.

The peripheral nerve stimulation of an individual patient results particularly advantageously from a simple matrix multiplication of a first matrix, which represents an individual patient stimulation model, and a second matrix, which represents a vector potential that actually occurs on an area surrounding the patient, wherein the position of the patient is already taken into account when calculating this vector potential.

A vector potential acting on the patient may be distributed on a cylindrical surface. This cylindrical surface surrounds the patient and is in alignment with the aforementioned virtual interface cylinder for determining patient stimulation. However, depending on the patient's position in the scanning unit, the relative position of the two cylinders in the axial direction may vary. The cylindrical surface covers the complete space that is accessible for the patient. To get the PNS response at an arbitrary position in the bore (the space) where the patient takes place in the MR scan unit, one has to multiply the unit vector potential in the elements of the interface cylinder by the vector potential created this position by a unit gradient current, which finally has to be multiplied by the gradient current of the actual pulse. To get this, the above-mentioned long cylindrical surface is defined. On this cylindrical surface, the vector potential is calculated for each gradient axis, using a unit gradient current. Both data sets, the PNS response as a function of the element vector potentials on the interface cylinder and the vector potential on the cylindrical surface, created by a unit gradient current in the gradient coil, are stored in a data memory. The vector potential is stored for each of the gradient axis. For example, this is done for an existing gradient system in advance in a factory.

In the context of the method for determining a peripheral nerve stimulation during MR imaging of a patient in a MR scanning unit for a MR pulse sequence, the distribution of the vector potential acting on the patient may be calculated for each of the three gradient axes. All components of the magnetic field acting on a patient are advantageously taken into account for calculating the peripheral stimulation, so that the result corresponds to the actual boundary conditions of a MR imaging.

A patient model may be selected for individual MR imaging by comparing patient data with the candidate models. A selection of a suitable patient model, which represents an individual response behavior of a patient, may advantageously be selected based on individual patient parameters.

In the event that none of the candidate models corresponds to the patient data with sufficient accuracy or may be assigned to these patient data with sufficient accuracy, an interpolation between two candidate models and an interpolated candidate model may be generated as a patient model. Advantageously, an interpolation improves the accuracy of a calculation of a peripheral stimulation of a patient, whereby the amount of data stored in the database need not be too large. The interpolations for the vector potential as well as for the peripheral stimulation values related to a unit vector potential are particularly advantageous relatively robust compared to interpolations in conventional methods, since the two variables, e.g., the vector potential and the stimulation values may not show any sudden changes.

BRIEF DESCRIPTION OF THE DRAWINGS

The disclosure is explained in more detail below with reference to the attached figures based on exemplary embodiments, in which:

FIG. 1 depicts a flowchart, which illustrates a method for determining a peripheral nerve stimulation during MR imaging of a patient in a MR scanning unit for a MR pulse sequence according to an embodiment.

FIG. 2 depicts a flowchart, which illustrates a gradient strength determination method according to an embodiment.

FIG. 6 depicts a schematic representation of a magnetic resonance imaging system according to an embodiment.

DETAILED DESCRIPTION

Figure 3:
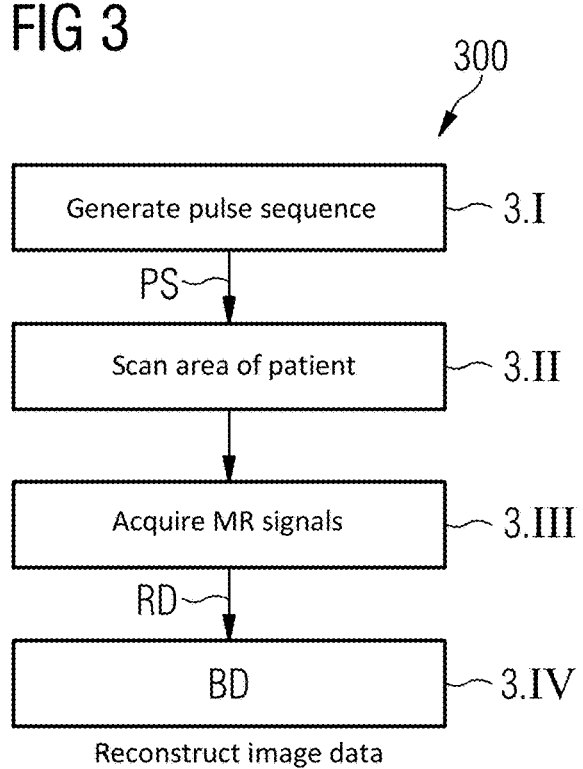
FIG. 3 depicts a flowchart, which illustrates a magnetic resonance imaging method according to an embodiment.

In order to make the object, technical solutions, and advantages of the present disclosure more apparent, the present disclosure will be further described in detail by way of embodiments hereinafter.

FIG. 1 shows a flow chart 100, which illustrates a method for determining peripheral nerve stimulation during MR imaging of a patient in a MR scanning unit for a MR pulse sequence according to an embodiment. In act 1.I, a number of models for candidate stimulations PNS ($A_e$ ($x_i$)) are first calculated for different patient parameter values PM as a function of a unit vector potential $A_e$ ($x_i$). Here, $x_i$ are the positions $x_i$ on a surface of a virtual interface cylinder IC around a patient area in a scanning unit. The patient parameter values can include, (e.g., the height of patient P, sex of the patient, fat distribution of the patient, muscle distribution of the patient, body mass index (BMI) of the patient, and the like). In accordance with this data, an individual model, (e.g., generated by machine learning, is used, with which a model-specific distribution of the peripheral candidate stimulation values PNS ($A_e$ ($x_i$)) is calculated. The distribution of the peripheral candidate stimulation values PNS ($A_e$ ($x_i$)) is calculated on the surface of a virtual interface cylinder IC surrounding a patient area. This calculation is still independent of the actual patient position because the calculation takes place independently of a specific patient P and is stored beforehand in a database. The candidate stimulation data PNS ($A_e$ ($x_i$)) are calculated using a grid, which includes values of the unit vector potential $A_e$ ($x_i$) evenly distributed over the interface cylinder IC and are stored in matrix form. Because the actual MR measurement, its protocol, and the position of the patient P in the scan unit of the MR system used for the MR measurement are not yet known when the candidate stimulation data PNS ($A_e$ ($x_i$)) are stored in advance, the calculation of the candidate stimulation values PNS ($A_e$ ($x_i$)) is based on unit vectors $A_e$ ($x_i$) of a vector potential of a magnetic field or a gradient magnetic field.

In act 1.II, depending on the known parameter values of a specific patient P, a suitable patient model $PM_{ind}$ is selected and thus the candidate stimulation data PNS ($A_e$ ($x_i$)) assigned to this patient model $PM_{ind}$ is selected as a suitable stimulation model $PNS_P$.

In act 1.III, a distribution of a vector potential A ($x_i$, $I_e$, $x_P$) of the gradient magnetic field generated during the MR imaging, acting on the patient P is calculated as a function of a unit gradient current $I_e$ for a determined position $x_P$ of the patient P in the MR scan unit 2 (see FIG. 6) and the individual patient model $PM_{ind}$. These values are also calculated on a long cylindrical surface CS, which has the same radius and circumference as the interface cylinder surface IC and is aligned with this when viewed in the axial direction, but already takes the patient position $x_P$ into account. The values of this vector potential A ($x_i$) are also calculated as discrete values over a grid over the cylindrical surface CS and stored in matrix form. The vector potential A ($x_i$) is calculated as a function of a unit gradient current $I_e$.

In act 1.IV, the two matrices PNS ($A_e$ ($x_i$)) and A ($x_i$) are finally multiplied with one another and also multiplied by a gradient current value in order to obtain the actual peripheral patient stimulation. The gradient current value for a MR protocol may, if necessary, be adjusted in such a way that the peripheral patient stimulation PNS does not exceed a predetermined value. The patient stimulation $PNS_{tot}$, which acts on the entire body and is related to a unit vector potential $A_e$ ($x_i$), is given by $$PNS_{tot} = \Sigma_{e,x_i} PNS(A_e(x_i)) \quad (1)$$

Here, e stands for the three gradient axes x, y, z. The value $x_i$ indicates the positions of the grid fields of the virtual interface cylinder IC. As already mentioned, this patient stimulation is multiplied by the matrix of the vector potential A($x_i$) and the gradient current value of a gradient pulse of a pulse sequence PS, which results in the already mentioned peripheral patient stimulation PNS.

FIG. 2 shows a flow chart 200, which illustrates a gradient strength determination method according to an embodiment. In act 2.I, a patient stimulation PNS dependent on a gradient strength I is calculated for a predetermined pulse sequence PS using the method illustrated in FIG. 1. Then, in act 2.II, a maximum gradient strength $I_{max}$ of the pulse sequence PS is determined, at which a permitted maximum patient stimulation $PNS_{max}$ is not exceeded. Finally, the pulse sequence PS is configured to the determined maximum gradient strength $I_{max}$, with gradient pulses and gradient currents being dimensioned accordingly in such a way that the determined limits are observed.

FIG. 3 shows a flow chart 300, which illustrates a magnetic resonance imaging method according to an embodiment. In act 3.I, a pulse sequence PS is generated, the gradients of which do not exceed a predetermined maximum patient stimulation $PNS_{max}$. This calculation is carried out by the gradient strength determination method shown in FIG. 2. The actual MR imaging process then begins in act 3.II, wherein an area FOV of a patient P to be examined is scanned by irradiating the generated pulse sequence PS. The magnetic resonance signals RD generated in the process are acquired in act 3.III and image data BD are reconstructed based on the acquired magnetic resonance signals RD.

Figure 4:
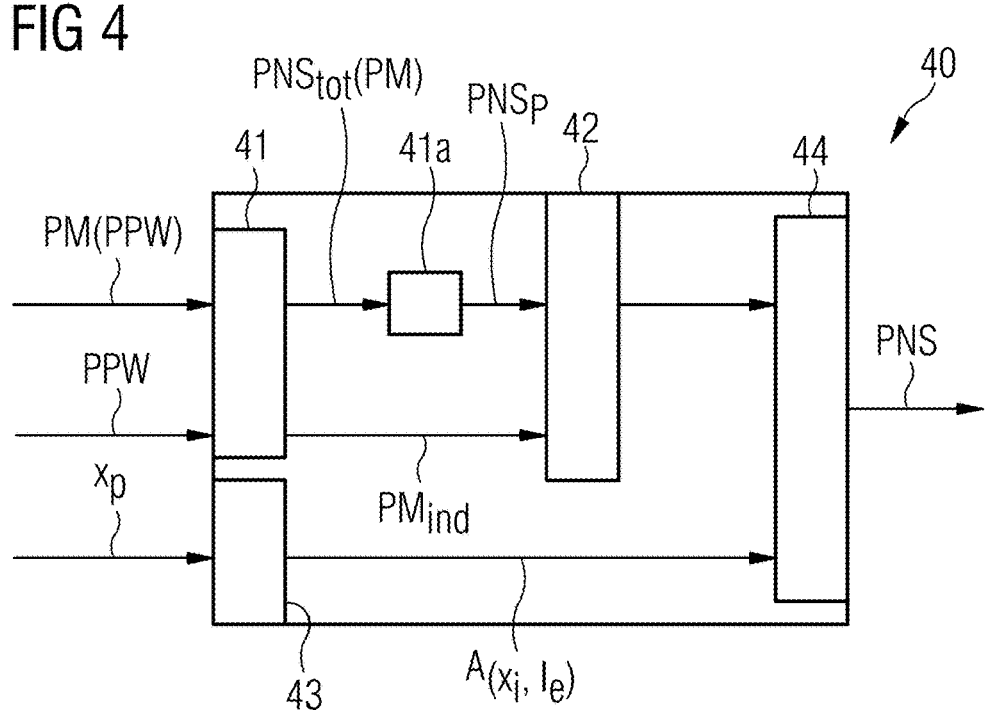
FIG. 4 depicts a block diagram, which illustrates a stimulation determination device according to an embodiment.

FIG. 4 illustrates a stimulation determination device 40 according to an embodiment. The stimulation determination device 40 also includes a candidate model determination unit 41 for determining a plurality of model-based candidate stimulations $PNS_{tot}$(PM) as a function of a unit vector potential $A_e$ ($x_i$) and candidate models PM (PPW) for different patients P with different patient parameter values PPW. The candidate models PM (PPW) are determined for a plurality of individual information for a measurement as well as different patient parameter values PPW. The candidate stimulations $PNS_{tot}$(PM) determined based on these candidate models PM (PPW) are subsequently stored in a data memory 41a. Part of the stimulation determination device 40 is also a selection unit 42 for selecting a model-based candidate data stimulation $PNS_{tot}$(PM) as a stimulation model $PNS_P$ for an individual patient P as a function of an individual patient model $PM_{ind}$ for this individual patient P, which is determined depending on the patient parameter values $PPW_{ind}$ of the individual patient P. The individual patient model $PM_{ind}$ is determined based on entered patient parameter values $PPW_{ind}$ by the candidate model determination unit 41 and forwarded to the selection unit 42. The stimulation determination device 40 also includes a vector potential determination unit 43 for determining a distribution of a vector potential A ($x_i$, $I_e$) that acts on the patient P and that is generated during the MR imaging by the gradient magnetic field B, as a function of a unit gradient current $I_e$ for an individual position $x_P$ of the individual patient P. Finally, the stimulation determination device 40 also includes a stimulation determination unit 44 for determining the nerve stimulation PNS of an individual patient P for the determined position $x_P$ based on a multiplication of the stimulation patient stimulation $PNS_{tot}$($PM_{ind}$, $A_e$) selected from the candidate stimulation models $PNS_{tot}$(PM) with the determined vector potential A ($x_i$, $I_e$) acting on the individual patient P and with a gradient current I of a gradient pulse GP of a MR pulse sequence.

Figure 5:
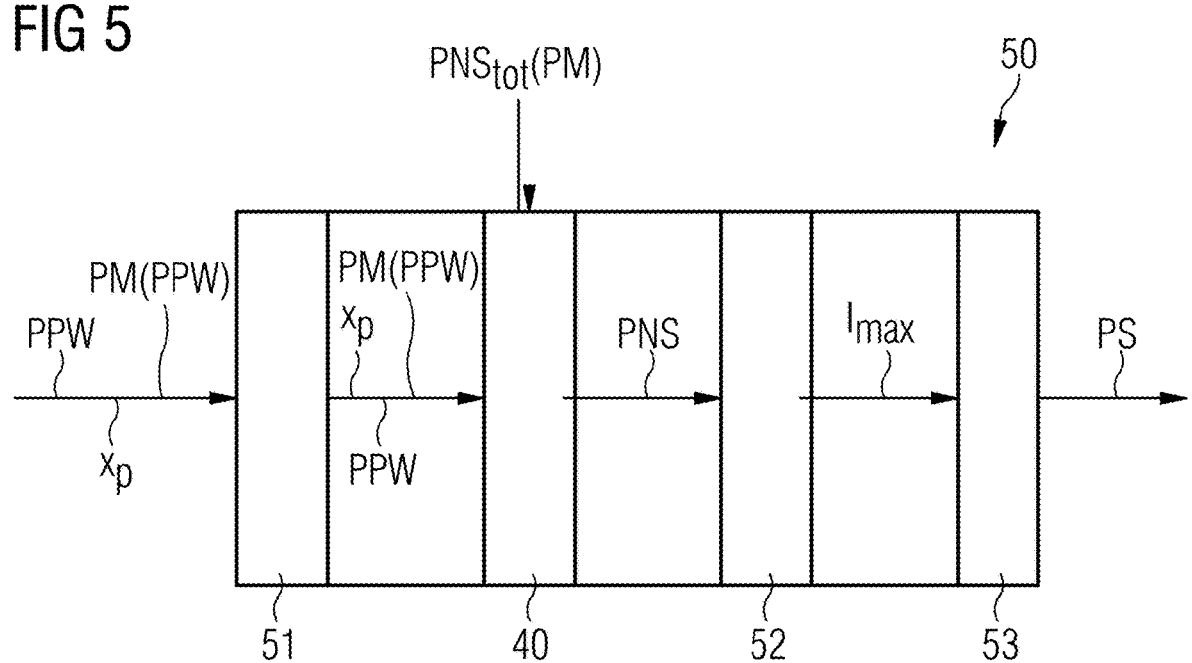
FIG. 5 depicts a block diagram, which illustrates a pulse sequence optimization device according to an embodiment.

FIG. 5 shows a pulse sequence optimization device 50 according to an embodiment. The pulse sequence optimization device 50 has an input interface 51 for receiving parameter values PPW of a patient P and a position $x_P$ of the patient P in a scan unit in a MR system. In addition, the pulse sequence optimization device 50 includes a stimulation determination device 40, as shown in FIG. 4. The nerve stimulation PNS determined by the stimulation determination device 40 is transmitted to a gradient strength determination unit 52, which is also part of the pulse sequence optimization device 50 and is set up to determine a maximum gradient current strength $I_{max}$ of a pulse sequence PS provided for a measurement, in which a permitted maximum patient stimulation $PNS_{max}$ is not exceeded, based on the determined patient stimulation PNS. The determined maximum gradient current strength $I_{max}$ is transmitted to a pulse sequence optimization unit 53 which is also included by the pulse sequence optimization device 50 and which is set up to adapt the pulse sequence PS of a MR measurement of an individual patient P to the determined maximum gradient current strength $I_{max}$. In particular, the amplitudes of the gradients of the pulse sequence PS is adapted in accordance with the determined maximum gradient current intensity $I_{max}$. This may lead to an increase in the amplitudes of the gradients as well as a decrease. An increase may lead to improved image quality, while by a decrease the maximum permitted patient stimulation is maintained.

A magnetic resonance system 1 (hereinafter referred to as "MR system" for short) is roughly schematically shown in FIG. 6. The MR system 1 includes the magnetic resonance scanner 2 with an examination zone 3 or patient tunnel in which a patient P, or here a patient or test person, for example, in whose body there is a certain organ, is on a couch 8, may be brought.

The magnetic resonance scanner 2 may be equipped with a basic field magnet system 4, a gradient system 6, a radio-frequency (RF) transmission antenna system 5, and a RF reception antenna system 7. In the embodiment shown, the RF transmission antenna system 5 is a whole-body coil permanently installed in the magnetic resonance scanner 2, whereas the RF reception antenna system 7 includes local coils to be arranged on the patient or test person (in FIG. 6 symbolized only by a single local coil). In principle, however, the whole-body coil may also be used as an RF receiving antenna system and the local coils as an RF transmitting antenna system, provided that these coils may each be switched to different modes of operation.

The MR system 1 also has a central control device 13, which is used to control the MR system 1. This central control device 13 includes a sequence control unit 14 for pulse sequence control. This is used to control the sequence of high-frequency pulses (RF pulses) and gradient pulses depending on a selected imaging sequence PS. Such an imaging sequence may be specified within a measurement or control protocol PR. Different control protocols PR for different measurements may be stored in a memory 19 and may be selected by an operator (and changed if necessary) and then used to carry out the measurement. Before the control protocols PR are sent to the sequence control unit 14, they are sent to a pulse sequence optimization device 50 for optimization. The pulse sequence optimization device 50 modifies gradient parameters in a received protocol PR or the pulse sequence PS based thereon, as explained in connection with FIG. 2 and FIG. 5 and sends the optimized control protocol $PR_{opt}$ to the sequence control unit 14 for pulse sequence control.

To output the individual RF pulses, the central control device 13 has a high-frequency transmission device 15, which generates the RF pulses, amplifies the RF pulses, and feeds the RF pulses into the RF transmission antenna system 5 via a suitable interface (not shown in detail). To control the gradient coils of the gradient system 6, the control device 13 has a gradient system interface 16. The sequence control unit 14 communicates in a suitable manner, (e.g., by sending out sequence control data SD), with the high-frequency transmission device 15 and the gradient system interface 16 for sending out the pulse sequences PS. The control device 13 also has a high-frequency receiving device 17 (likewise communicating in a suitable manner with the sequence control unit 14) in order to acquire magnetic resonance signals, (e.g., raw data RD), in a coordinated manner, which magnetic resonance signals have been received from the RF transmitting antenna system 7. A reconstruction unit 18 takes over the acquired raw data RD and reconstructs the MR image data BD therefrom. These image data BD may then be stored in a memory 19, for example.

The central control device 13 may be operated via a terminal with an input unit 10 and a display unit 9, via which the entire MR system 1 may thus also be operated by an operator. MR images may also be displayed on the display unit 9, and measurements may be planned and started using the input unit 10, if necessary in combination with the display unit 9, and in particular suitable control protocols with suitable measurement sequences such as explained above may be selected and modified, if necessary.

The MR system 1 and, in particular, the control device 13 may also have a large number of other components that are not shown in detail here but may be present on such devices, such as a network interface to connect the entire system to a network and to be able to exchange raw data RD and/or image data BD or parameter maps, but also other data, such as patient-relevant data or control protocols.

How suitable raw data RD may be acquired by irradiating RF pulses and generating gradient fields and how MR images BD may be reconstructed therefrom is known in principle to the person skilled in the art and is not explained in more detail here. There are also a wide variety of measurement sequences, such as EPI sequences, GRE measurement sequences, or TSE measurement sequences for generating dynamic or static images, which are in principle well known to the person skilled in the art.

Figure 7:
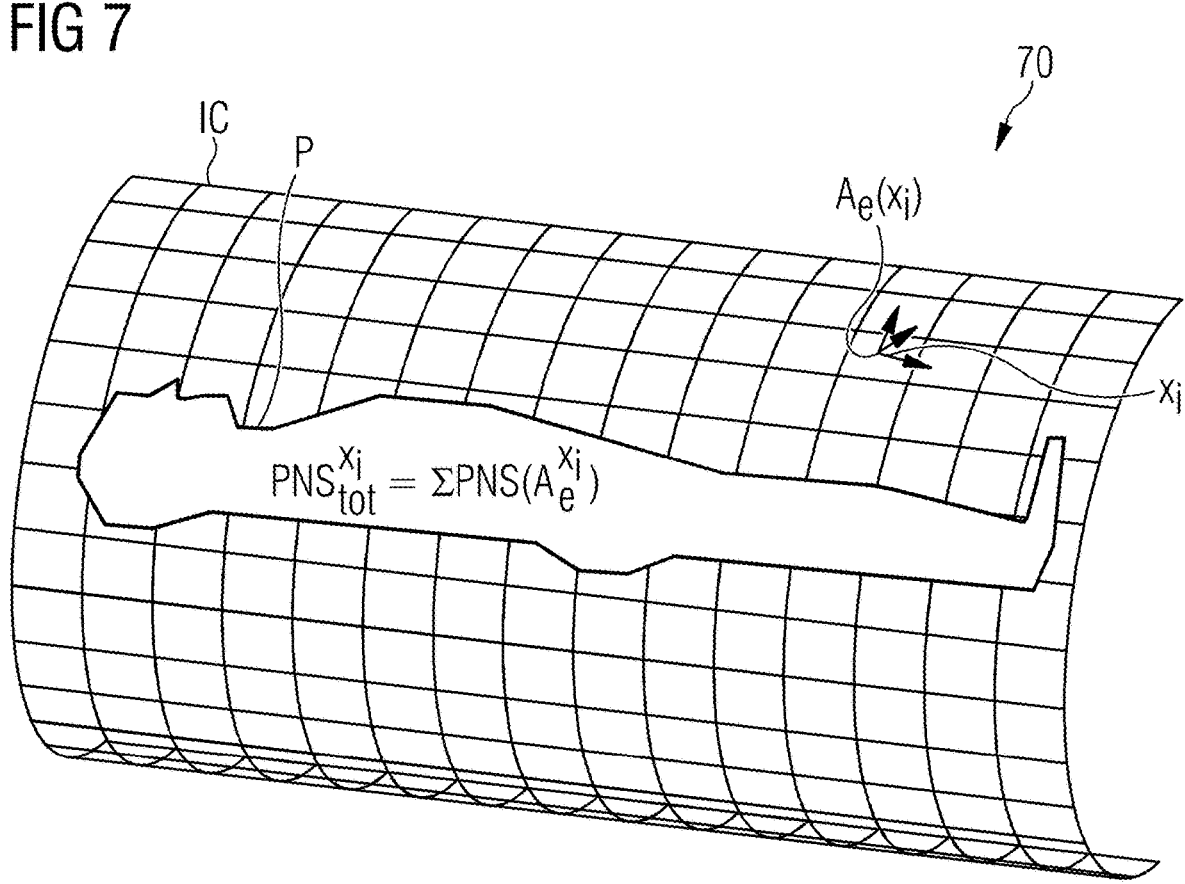
FIG. 7 depicts a representation of the concept of the virtual cylindrical interface surface for calculating a PNS response to a unit vector potential according to an embodiment.

FIG. 7 shows a schematic representation 70 of the calculation of a candidate stimulation $PNS_{tot}(PM)$. Stimulation values PNS ($A_e(x_i)$) are calculated for an individual candidate model $PM_{ind}$ on an interface cylinder surface IC as a function of unit vector potentials $A_e(x_i)$. If such a candidate model is selected for a MR imaging for an individual patient P, the stimulation values PNS ($A_e(x_i)$) are multiplied with a vector potential A ($x_i$) that is dependent on the patient position $x_P$ of the specific patient P in a MR scan unit.

Figure 8:
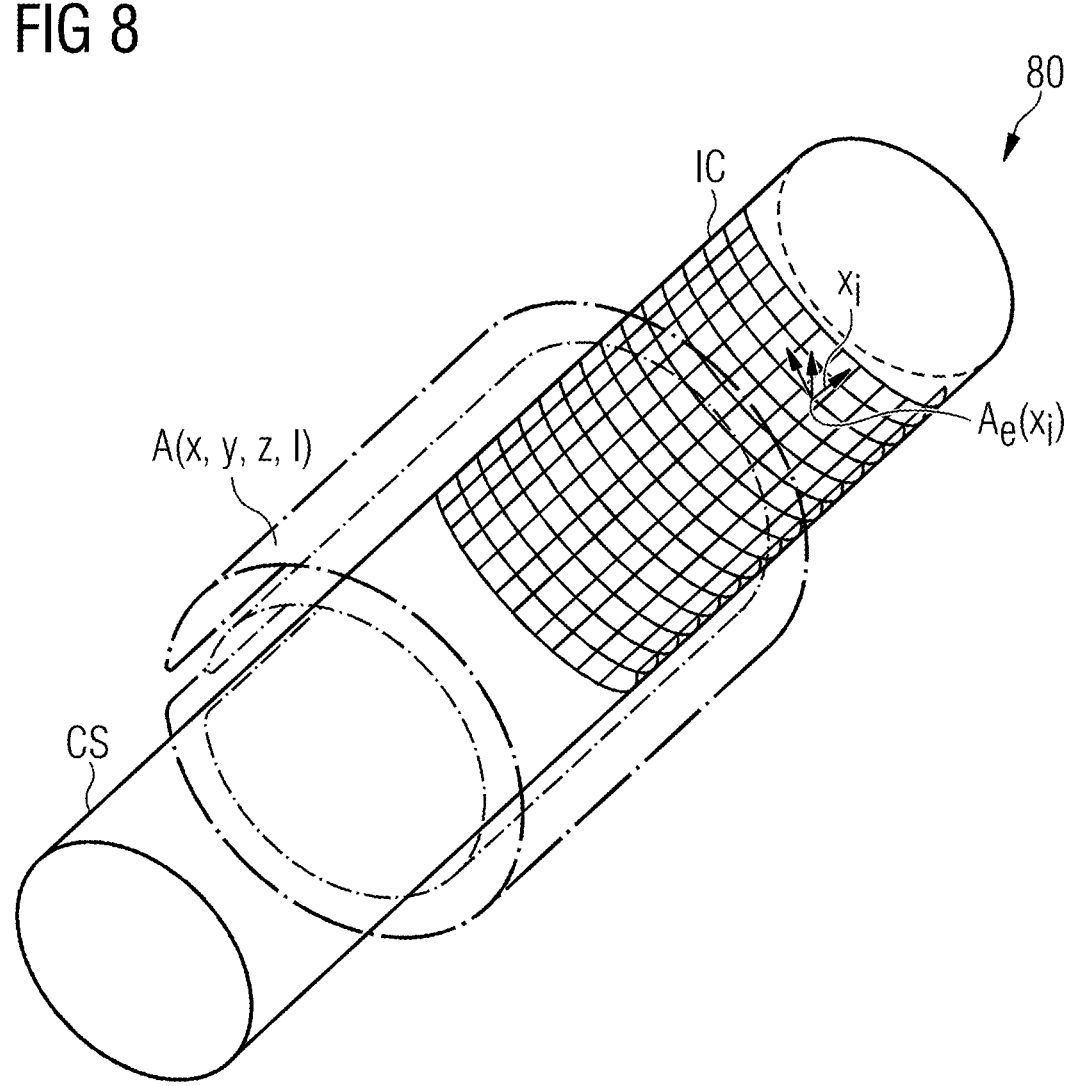
FIG. 8 depicts a representation of the concept of the cylindrical surface for calculating a vector potential based on a unit gradient current in connection with the virtual cylindrical interface surface illustrated in FIG. 7.

This process is illustrated in FIG. 8 in a schematic representation 80. A vector potential A (x, y, z, I) of a magnetic field, as it is formed in a scanning unit during MR imaging in a recording area around a cylindrical surface CS, is shown there. Furthermore, an interface cylinder surface IC is drawn in, which has grid areas to which unit vectors $A_e(x_i)$ of the vector potential A (x, y, z, I) are assigned.

Finally, it is pointed out once again that the methods and devices described above are exemplary embodiments of the disclosure and that the disclosure may be varied by a person skilled in the art without departing from the scope of the disclosure, insofar as it is specified by the claims. The method and the magnetic resonance imaging system were explained primarily based on an application for recording medical image data. However, the disclosure is not restricted to use in the medical field, but rather the disclosure may also be applied to the recording of images for other purposes. For the sake of completeness, it is also pointed out that the use of the indefinite article "a" or "an" does not exclude the possibility that the relevant features may also be present several times. Likewise, the term "unit" does not exclude that it includes several components, which may also be spatially distributed.

It is to be understood that the elements and features recited in the appended claims may be combined in different ways to produce new claims that likewise fall within the scope of the present disclosure. Thus, whereas the dependent claims appended below depend from only a single independent or dependent claim, it is to be understood that these dependent claims may, alternatively, be made to depend in the alternative from any preceding or following claim, whether independent or dependent, and that such new combinations are to be understood as forming a part of the present specification.

While the present disclosure has been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description.

REFERENCE NUMBERS 1 magnetic resonance system
2 MR scanning unit
3 examination zone
4 basic field magnet system
5 RF transmission antenna system
6 gradient system
7 RF receiving antenna system
8 bed
9 Display unit
10 input unit
13 central control device
14 sequence control unit
15 radio frequency transmitter
16 gradient system interface
17 radio frequency receiving equipment
18 reconstruction unit
19 memory
40 stimulation detection device
41 candidate model determination unit
41a data storage
42 selection unit
43 vector potential determination unit
44 stimulation determination unit
50 pulse sequence optimization device
51 input interface
52 gradient strength determination unit
53 pulse sequence optimization unit
70 illustration of the calculation of a candidate stimulation
80 schematic representation of a vector potential
A ($x_i$) vector potential
$A_e$ ($x_i$) unit vector
A ($x_i$, $I_e$, $x_p$) vector potential acting on the patient as a function of a unit gradient current and the position of a patient
A (x, y, z, I) current-dependent vector potential
BD image data
CS cylindrical surface
GP gradient pulse
IC interface cylinder
$I_e$ unit gradient current
I gradient current
P patient
PM patient parameter value
$PM_{ind}$ patient model
PM (PPW) candidate model
PNS ($A_e$ ($x_i$)) model for candidate stimulations
$PNS_{max}$ maximum patient stimulation
$PNS_P$ stimulation model for an individual patient
$PNS_{tot}$ patient stimulation
$PNS_{tot}$ (PM) model-based candidate stimulation
$PNS_{tot}$ ($PM_{ind}$, $A_e$) selected patient stimulation
PPW parameter value of a patient
$PPW_{ind}$ patient parameter value of an individual patient
PR measurement or control protocol
$PR_{opt}$ optimized control protocol
PS pulse sequence
RD magnetic resonance signals/raw data
SD sequence control data
$x_p$ position

The invention claimed is:

1. A method for determining a peripheral nerve stimulation during a magnetic resonance (MR) imaging of a patient in a MR scan unit for a MR pulse sequence, the method comprising:

determining, by a stimulation determining device, a plurality of model-based candidate stimulations as a function of a unit vector potential of a gradient magnetic field generated during the MR imaging and candidate models for different object parameter values;

selecting, by the stimulation determining device, a model-based candidate stimulation as a stimulation model for the patient depending on an individual patient model for the patient, which is determined depending on the object parameter values of the patient;

determining, by the stimulation determining device, a distribution of a vector potential of the gradient magnetic field acting on the patient, generated during MR imaging, as a function of a unit gradient current for a determined position of the patient in the MR scan unit; and determining, by the stimulation determining device, the peripheral nerve stimulation of the patient for the determined position based on the selected model-based candidate stimulation, the determined vector potential acting on the patient, and a gradient current of a gradient pulse of the MR pulse sequence.

2. The method of claim 1, wherein, in the determining of the model-based candidate stimulations, a virtual interface cylinder is placed around a candidate model and location-dependent stimulation values for partial surfaces of the virtual interface cylinder are determined.

3. The method of claim 2, wherein the determined model-based candidate stimulations are determined based on a sum of the plurality of model-based candidate stimulations assigned to the partial surfaces of the virtual interface cylinder.

4. The method of claim 1, wherein the individual patient model is generated as a function of one or more individual object parameter values comprising: a size of the patient, a weight of the patient, a fat distribution of the patient, a muscle distribution of the patient, a body mass index of the patient, a sex of the patient, or combinations thereof.

5. The method of claim 1, wherein the stimulation of the patient is determined for the determined position by multiplication of: (1) the selected model-based candidate stimulation, (2) the determined vector potential acting on the patient, and (3) the gradient current of the gradient pulse of the MR pulse sequence.

6. The method of claim 1, wherein the distribution of a vector potential acting on the patient is arranged on a cylindrical surface around the patient.

7. The method of claim 1, wherein the individual patient model is selected for individual MR imaging by comparing individual patient data with the candidate models.

8. The method of claim 7, wherein the individual patient data comprises the object parameter values of the patient.

9. The method of claim 7, wherein, when none of the candidate models correspond to the individual patient data with sufficient accuracy, an interpolation between two candidate models is performed and an interpolated candidate model is generated as a patient model.

10. The method of claim 1, further comprising:
determining a maximum gradient strength of the MR pulse sequence, at which an allowed maximum patient stimulation is not exceeded; and
adapting the MR pulse sequence to the determined maximum gradient strength.

11. The method of claim 10, further comprising:
generating the MR pulse sequence, gradients of which do not exceed the allowed maximum patient stimulation;
stimulating an area to be examined of the patient using the generated MR pulse sequence;
acquiring magnetic resonance signals; and
reconstructing image data based on the acquired magnetic resonance signals.

12. A stimulation determination device comprising:
a candidate model determination unit configured to determine a plurality of model-based candidate stimulations as a function of a unit vector potential and candidate models for different patients;
a selection unit configured to select a model-based candidate stimulation as a stimulation model for a patient depending on an individual patient model for the patient, which is determined depending on object parameter values of the patient;
a vector potential determination unit configured to determine a distribution of a vector potential of a gradient magnetic field, acting on the patient, generated during magnetic resonance (MR) imaging as a function of a unit gradient current for a determined position of the patient in a MR scan unit; and
a stimulation determination unit configured to determine a nerve stimulation of the patient for the determined position based on the selected model-based candidate stimulation, the determined vector potential acting on the patient, and a gradient current of a gradient pulse of a MR pulse sequence.

13. A pulse sequence optimization device comprising:
an input interface configured to receive parameter values of a patient and a position of the patient in a scanner of a magnetic resonance (MR) system;
a stimulation determining device configured to:
determine a plurality of model-based candidate stimulations as a function of a unit vector potential and candidate models for different patients;
select a model-based candidate stimulation as a stimulation model for the patient depending on an individual patient model for the patient, which is determined depending on object parameter values of the patient;
determine a distribution of a vector potential of a gradient magnetic field, acting on the patient, generated during MR imaging as a function of a unit gradient current for a determined position of the patient in the scanner of the MR system; and
determine a nerve stimulation of the patient for the determined position based on the selected model-based candidate stimulation, the determined vector potential acting on the patient, and a gradient current of a gradient pulse of a pulse sequence;
a gradient strength determination unit configured to determine a maximum gradient current strength of the pulse sequence, in which an allowed maximum patient stimulation is not exceeded, based on the determined patient stimulation; and
a pulse sequence optimization unit configured to adapt the pulse sequence to the determined maximum gradient strength based on the determined maximum gradient current strength.

14. A magnetic resonance (MR) imaging system comprising:
a high-frequency transmission system;
a gradient system;
a control device configured to control the high-frequency transmission system and the gradient system based on a pulse sequence in order to carry out a desired measurement; and
a pulse sequence optimization device configured to adapt the pulse sequence to a patient, the pulse sequence optimization device comprising:
an input interface configured to receive parameter values of the patient and a position of the patient in a scanner of the MR imaging system;
a stimulation determining device configured to:
determine a plurality of model-based candidate stimulations as a function of a unit vector potential and candidate models for different patients;
select a model-based candidate stimulation as a stimulation model for the patient depending on an individual patient model for the patient, which is determined depending on object parameter values of the patient;
determine a distribution of a vector potential of a gradient magnetic field, acting on the patient, generated during MR imaging as a function of a unit gradient current for a determined position of the patient in the scanner of the MR imaging system; and
determine a nerve stimulation of the patient for the determined position based on the selected model-based candidate stimulation, the determined vector potential acting on the patient, and a gradient current of a gradient pulse of the pulse sequence;
a gradient strength determination unit configured to determine a maximum gradient current strength of the pulse sequence, in which an allowed maximum patient stimulation is not exceeded, based on the determined nerve stimulation of the patient; and
a pulse sequence optimization unit configured to adapt the pulse sequence to the determined maximum gradient current strength.

15. The stimulation determination device of claim 12, wherein, in the determination of the model-based candidate stimulations, a virtual interface cylinder is configured to be placed around a candidate model and location-dependent stimulation values for partial surfaces of the virtual interface cylinder are determined.

16. The stimulation determination device of claim 15, wherein the determined model-based candidate stimulations are determined based on a sum of the plurality of model-based candidate stimulations assigned to the partial surfaces of the virtual interface cylinder.

17. The stimulation determination device of claim 12, wherein the stimulation of the patient is configured to be determined for the determined position by multiplication of: (1) the selected model-based candidate stimulation, (2) the determined vector potential acting on the patient, and (3) the gradient current of the gradient pulse of the MR pulse sequence.

18. The stimulation determination device of claim 12, wherein the individual patient model is configured to be selected for individual MR imaging by comparing individual patient data with the candidate models.

19. The stimulation determination device of claim 18, wherein, when none of the candidate models correspond to the individual patient data with sufficient accuracy, an interpolation between two candidate models is configured to be performed and an interpolated candidate model is configured to be generated as a patient model.

* * * * *